United States Patent
Bastek et al.

[11] Patent Number: 5,985,836
[45] Date of Patent: Nov. 16, 1999

[54] ALPHA-1 PROTEINASE INHIBITOR BINDING PEPTIDES

[75] Inventors: Patrick D. Bastek, Chapel Hill; John M. Lang, Raleigh; George A. Baumbach, Knightdale; Ruben G. Carbonell, Raleigh, all of N.C.

[73] Assignee: Bayer Corporation, Berkeley, Calif.

[21] Appl. No.: 09/127,574

[22] Filed: Jul. 31, 1998

[51] Int. Cl.$^6$ .......................... A61K 38/00; A61K 38/02; C07K 5/00; C07K 7/00
[52] U.S. Cl. .............................................. 514/17; 530/329
[58] Field of Search ................................. 514/17; 530/329

[56] References Cited

FOREIGN PATENT DOCUMENTS

| | | | |
|---|---|---|---|
| 9535306 | 12/1995 | WIPO | .............................. C07K 1/16 |
| 9709350 | 3/1997 | WIPO | .............................. C07K 14/81 |

*Primary Examiner*—Avis M. Davenport
*Attorney, Agent, or Firm*—Michael J. Beck; James A. Giblin

[57] ABSTRACT

Peptides which bind to alpha-1 Proteinase inhibitor (AlPI) are disclosed. The peptides have an available AlPI binding domain which may be any of the following preferred sequences: Val Ile Trp Leu Val Arg, Ile Ile Trp Leu Tyr Lys, Arg Tyr Arg Ile Phe Ile, Arg Ala Phe Trp Tyr Ile, Arg Phe Ile Tyr Tyr Thr, Tyr Lys Phe Arg Phe Trp, Leu Ile Val His Arg Trp, Pro Tyr Trp Ile Val Arg, Ala Arg Trp Tyr Ile His, Gln Tyr His Phe Trp Tyr, Arg Leu Trp Arg Tyr Gly, Val Ile Tyr Leu Val Arg, Val Ile Phe Leu Val Arg, Lys Ile Phe Leu Val Arg, Arg Ile Phe Leu Val Arg, His Ile Phe Leu Val Arg, Arg Val Leu Phe Ile Val, or Arg Val Leu Phe Ile His (SEQ ID NOS: 1–8, 10, 11, 15, 36, 37, 45, 46, 47, 61, and 62 respectively). A method of using peptides having these available binding domains in an affinity chromatography process to purify AlPI is described.

6 Claims, 3 Drawing Sheets

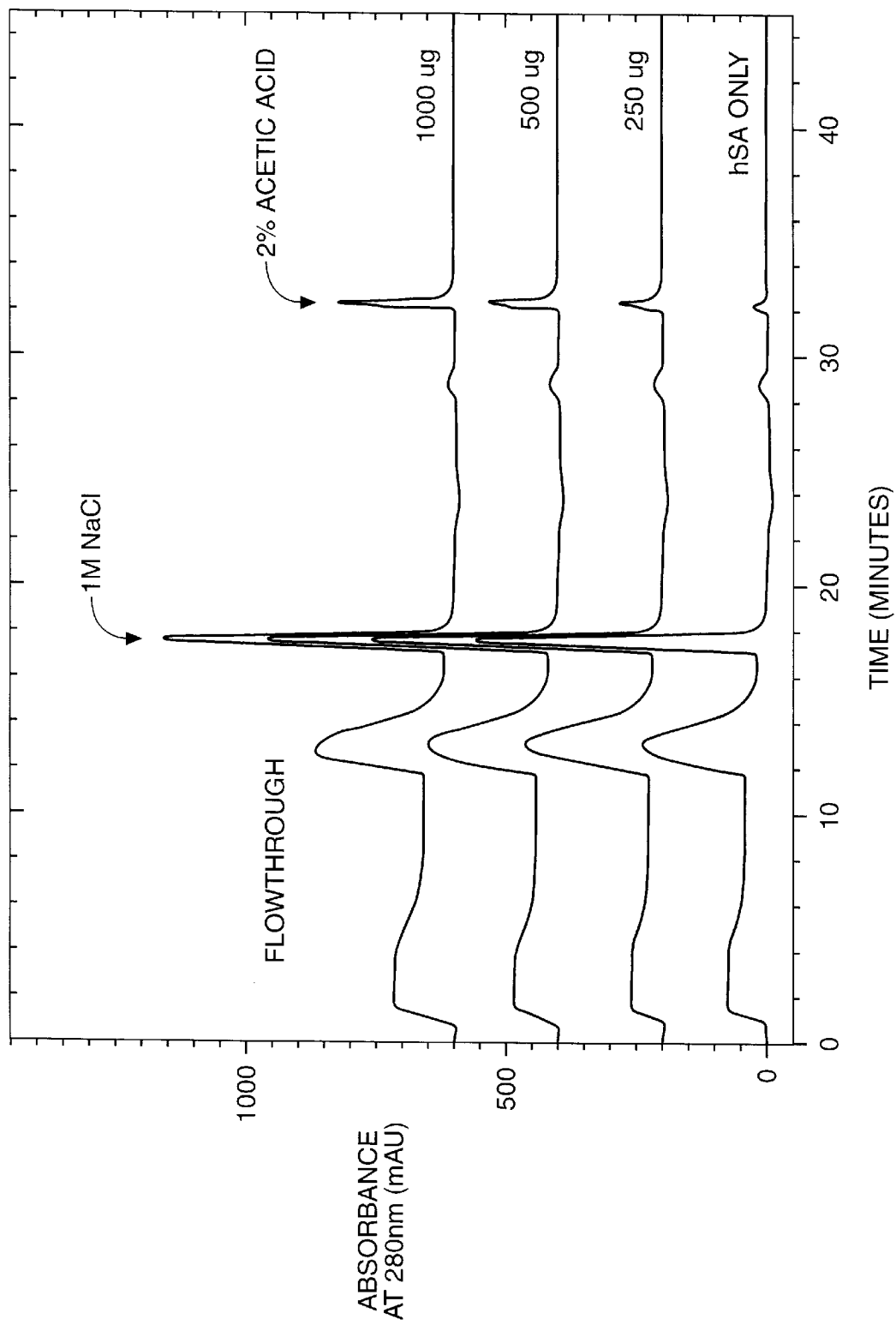
FIG._1

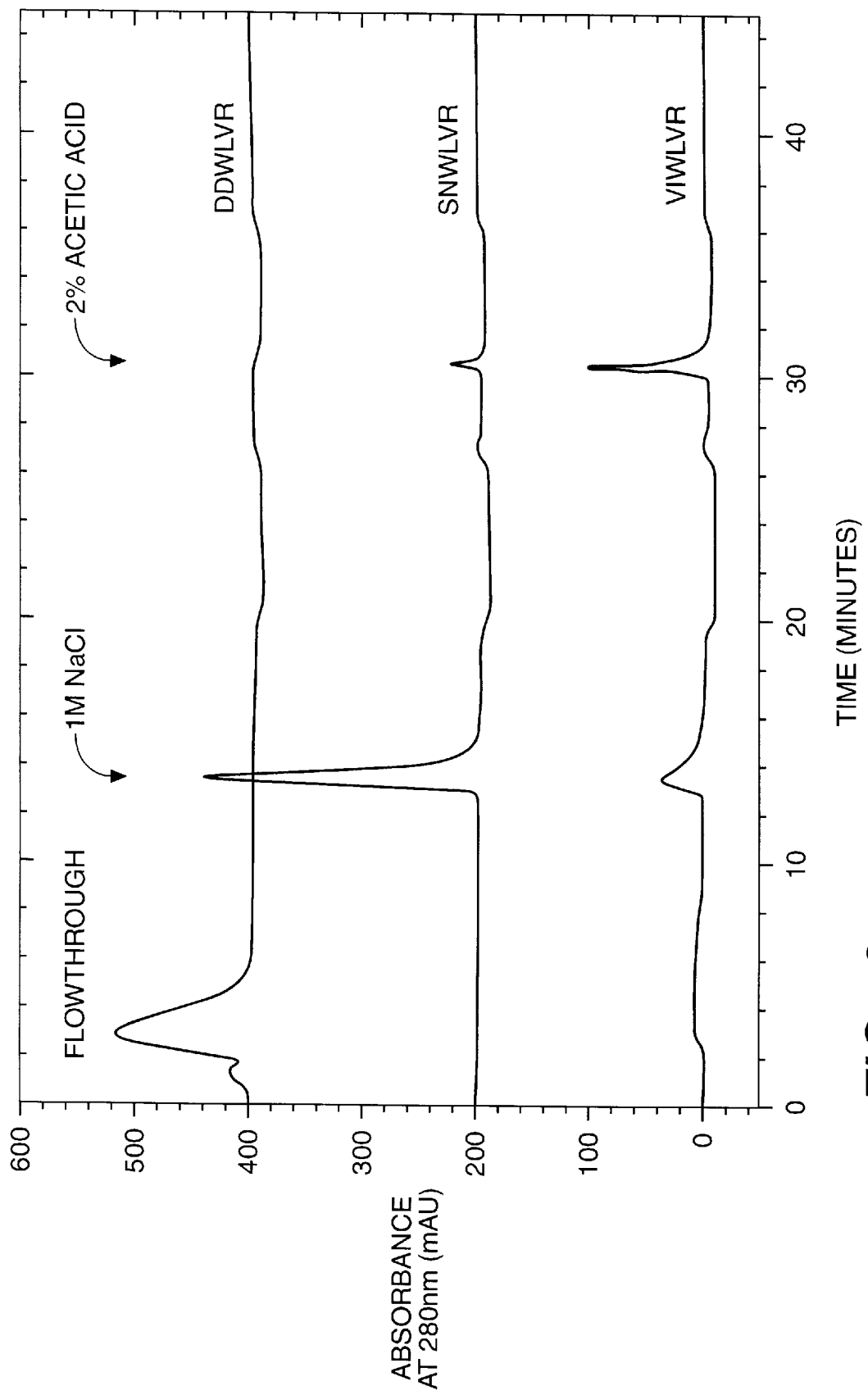
FIG._2

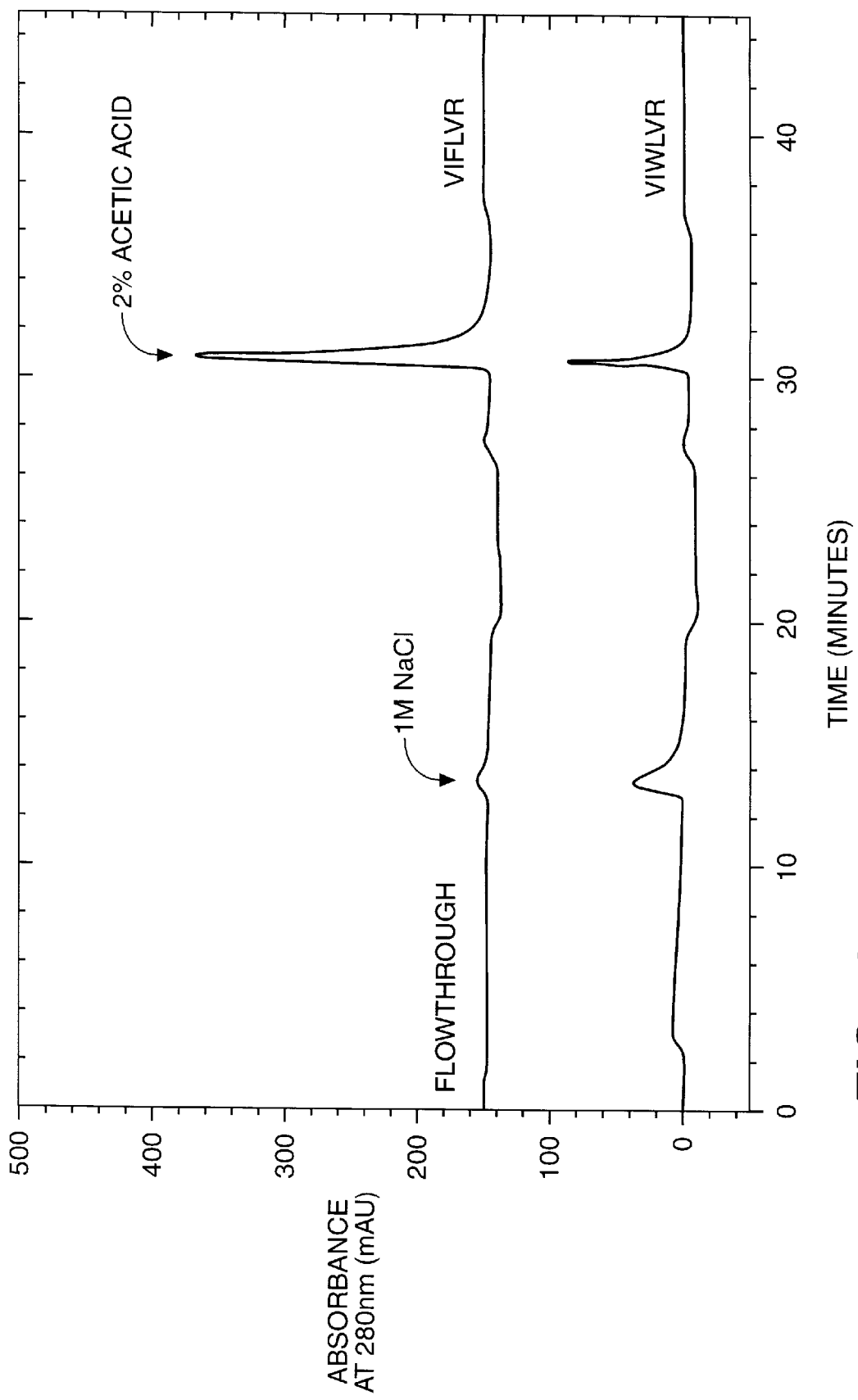
FIG._3

SEQUENCE LISTING

```
<160> NUMBER OF SEQ ID NOS: 62

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 1

Val Ile Trp Leu Val Arg
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 2

Ile Ile Trp Leu Tyr Lys
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 3

Arg Tyr Arg Ile Phe Ile
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 4

Arg Ala Phe Trp Tyr Ile
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 5

Arg Phe Ile Tyr Tyr Thr
  1               5

<210> SEQ ID NO 6
<211> LENGTH: 6
```

```
<212> TYPE: PRT
<213> ORGANISM: Artificial Sequence
<220> FEATURE:
<223> OTHER INFORMATION: Description of Artificial Sequence:Synthetic

<400> SEQUENCE: 6

Tyr Lys Phe Arg Phe Trp
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 7

Leu Ile Val His Arg Trp
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 8

Pro Tyr Trp Ile Val Arg
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 9

Trp Lys Leu Trp Arg Trp
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 10

Ala Arg Trp Tyr Ile His
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 11

Gln Tyr His Phe Trp Tyr
 1               5

<210> SEQ ID NO 12
<211> LENGTH: 6
<212> TYPE: PRT
<213> ORGANISM: Artificial Sequence
```

<220> FEATURE:
<223> OTHER INFORMATION: Description of Artificial Sequence:Synthetic

<400> SEQUENCE: 12

Trp Ser Ser Lys Arg Tyr
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 13

Trp Ile Lys Trp Thr Lys
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 14

Arg Arg Lys Tyr Leu Trp
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 15

Arg Leu Trp Arg Tyr Gly
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 16

Asn Trp Lys Arg Val Arg
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 17

Ile Trp Arg Lys Tyr Ser
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Synthetic

```
<400> SEQUENCE: 18

Ile Lys Arg Tyr Tyr Asn
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 19

Ile Lys Arg Tyr Tyr Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 20

Ser Asp Trp Leu Val Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 21

Asp Asp Trp Leu Val Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 22

Asn Asp Trp Leu Val Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 23

Asp Ser Trp Leu Val Arg
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 24
```

```
Asp Asn Trp Leu Val Arg
  1               5
```

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 25

```
Asp His Trp Leu Val Arg
  1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 26

```
His Asp Trp Leu Val Arg
  1               5
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 27

```
Ser Ser Trp Leu Val Arg
  1               5
```

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 28

```
Ser Asn Trp Leu Val Arg
  1               5
```

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 29

```
Ser His Trp Leu Val Arg
  1               5
```

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 30

```
His Ser Trp Leu Val Arg
```

```
<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 31

His Asn Trp Leu Val Arg
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 32

His His Trp Leu Val Arg
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 33

Asn His Trp Leu Val Arg
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 34

Asn Ser Trp Leu Val Arg
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 35

Asn Asn Trp Leu Val Arg
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 36

Val Ile Tyr Leu Val Arg
 1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 37

Val Ile Phe Leu Val Arg
 1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 38

Val Ile Leu Leu Val Arg
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 39

Val Ile Val Leu Val Arg
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 40

Val Ile Asn Leu Val Arg
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 41

Val Ile Asp Leu Val Arg
 1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 42

Val Ile Ser Leu Val Arg
 1               5

<210> SEQ ID NO 43
```

```
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 43

Val Ile Ala Leu Val Arg
 1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 44

Val Ile Arg Leu Val Arg
 1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 45

Lys Ile Phe Leu Val Arg
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 46

Arg Ile Phe Leu Val Arg
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 47

His Ile Phe Leu Val Arg
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 48

Ser Ile Phe Leu Val Arg
 1               5

<210> SEQ ID NO 49
<211> LENGTH: 6
<212> TYPE: PRT
```

<213> ORGANISM: Artificial Sequence
<220> FEATURE:
<223> OTHER INFORMATION: Description of Artificial Sequence:Synthetic

<400> SEQUENCE: 49

Ala Ile Phe Leu Val Arg
 1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 50

Asn Ile Phe Leu Val Arg
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 51

Asp Ile Phe Leu Val Arg
 1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 52

Val His Phe Leu Val Arg
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 53

Val Arg Phe Leu Val Arg
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 54

Val Lys Phe Leu Val Arg
 1               5

<210> SEQ ID NO 55
<211> LENGTH: 6
<212> TYPE: PRT
<213> ORGANISM: Artificial Sequence
<220> FEATURE:

```
<223> OTHER INFORMATION: Description of Artificial Sequence:Synthetic

<400> SEQUENCE: 55

Val Ala Phe Leu Val Arg
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 56

Val Ile Phe Ala Val Arg
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 57

Val Ile Phe Leu Ala Arg
 1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 58

Val Ile Phe Leu Phe Arg
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 59

Val Ile Phe Leu Tyr Arg
 1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 60

Val Ile Phe Leu Val Ala
 1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence:Synthetic
```

```
<400> SEQUENCE: 61

Arg Val Leu Phe Ile Val
 1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 62

Arg Val Leu Phe Ile His
 1               5
```

ALPHA-1 PROTEINASE INHIBITOR BINDING PEPTIDES

BACKGROUND OF THE INVENTION

1. Field:

This invention is concerned generally with identifying protein-ligand interactions, and specifically with peptide ligands which bind alpha-1 proteinase inhibitor (A1PI) and which may be used in a method for the affinity purification of A1PI.

2. Prior Art:

A1PI is a (gycoprotein with a molecular weight of 53,000 Daltons. A1PI is an inhibitor of proteases such as trypsin, chymotrypsin, and elastase. A current therapeutic use of A1PI is the inhibition of lymphocyte elastase in the lungs. When A1PI is not present in sufficient quantities to regulate elastase activity due to genetic deficiency, the elastase breaks down lung tissue, resulting in lung tissue damage and emphysema. A1PI replacement therapy has been successfully used for treatment of this form of emphysema.

While the A1PI gene has been transformed and expressed in microorganisms, cell lines, and sheep, a satisfactory recombinant product has yet to be produced. Human plasma is currently the only approved source of therapeutic A1PI. To date a practical process which gives both high yield and high purity A1PI has not been available.

Various methods of purifying A1PI from human plasma have been described. Bollen et al., U.S. Pat. No. 4,629,567 (1986) used five different chromatography steps to purify A1PI from yeast, *E. coli*, and human plasma. The five steps involved DEAE ion exchange, thio-disulfide exchange, heparin affinity, zinc-chelate chromatography, and amino hexyl ion exchange. No purity and yield data were shown.

Novika et al. (1989) reported isolation methods from the by-products of the manufacture of blood products. They used affinity, DEAE cellulose, and gel filtration chromatographies. The purity and yield data were not available.

Podiarenc et al. (1989) reported a single step procedure for isolation of A1PI from human plasma using affinity chromatography with monoclonal antibodies. A1PI activity was increased 61.1 fold with a yield of 20%.

Burnouf et al. (1987) starting with plasma supernatant A (equivalent to Cohn Fraction II+III) used DEAE chromatography and size exclusion chromatography to produce an A1PI which was 80–90% pure (by SDS-PAGE) with a 36-fold increase in purity. Recovery was 65–70% from the supernatant A.

Hein et al. (1990) presented a process which employs Cohn Fraction IV-1 as the starting, material and utilized fractional precipitation with polyethylene glycol followed by anion exchange chromatography on DEAE Sepharose®. The final product has a purity of about 60% with 45% yield. Other similarly based purifications from Cohn Fractions I, II+III and IV-1 are presented in U.S. Pat. Nos. 4,379,087 (1983), 4,439,358 (1984), and 4,697,003 (1987) by Coan et al. and U.S. Pat. No. 4,656,254 (1987) by Shearer et al.

Dubin et al. (1990) have shown a two step chromatographic purification. First A1PI, C1 inhibitor, alpha-1 antichymotrypsin, and inter alpha-1 trypsin inhibitor were eluted from Blue Sepharose® and the A1PI was purified by gel filtration. Purity and yield data were not available.

Ballieux et al. (1993) purified an A1PI and proteinase-3 complex from purulent sputum using 4-phenlybutylamine affinity chromatography, cation exchange, and a final immunoaffinity step. The pH of the buffer used in the cation exchange step was 7.0. Under the conditions used, most of the sputum proteins bound to the resin, but A1PI and proteinase-3 passed through without binding.

Lebing et al., U.S. Pat. No. 5,610,285 (1997) purified A1PI from Cohn Fractions IV-1 and II+III by changing the solution conditions to low ionic strength and pH 6.0. Passing the mixture over a cation exchange chromatography resin bound other proteins, but allowed a purified fraction of A1PI to flow through the column.

Hwang et al., U.S. Pat. No. 5,616,693 (1997) purified A1PI from Cohn Fraction IV-1. The fraction was precipitated with polyethylene glycol to remove other proteins. Zinc chloride was then added to the supernatant to precipitate a crude A1PI fraction. The crude A1PI fraction was resolubilized and purified using an anion exchange chromatography step.

SUMMARY OF THE INVENTION

We have now discovered a group of peptides characterized by their ability to bind A1PI. The sequences of the more preferred peptides having available A1PI binding domains are Val-Ile-Phe-Leu-Val-Arg (SEQ ID NO:37), Val-Ile-Trp-Leu-Val-Arg (SEQ ID NO:1), and those presented in Table 1. We also describe a method of using the peptides in an affinity chromatography process to purify AlPI. The method comprises passing an AlPI containing solution over a substrate which has bound thereupon peptides disclosed herein, and then eluting the AlPI.

TABLE 1

A1PI Binding Peptide Sequences
Sequences returned from screening of hexameric peptide library with $^{14}$C-A1PI

| SEQ ID | Sequence | | | | | | Short-Hand |
|---|---|---|---|---|---|---|---|
| 1 | Val | Ile | Trp | Leu | Val | Arg | VIWLVR |
| 2 | Ile | Ile | Trp | Leu | Tyr | Lys | IIWLYK |
| 3 | Arg | Tyr | Arg | Ile | Phe | Ile | RYRIFI |
| 4 | Arg | Ala | Phe | Trp | Tyr | Ile | RAFWYI |
| 5 | Arg | Phe | Ile | Tyr | Tyr | Thr | RFIYYT |
| 6 | Tyr | Lys | Phe | Arg | Phe | Trp | YKFRFW |
| 7 | Leu | Ile | Val | His | Arg | Trp | LIVHRW |
| 8 | Pro | Tyr | Trp | Ile | Val | Arg | PYWIVR |
| 9 | Trp | Lys | Leu | Trp | Arg | Trp | WKLWRW |
| 10 | Ala | Arg | Trp | Tyr | Ile | His | ARWYIH |
| 11 | Gln | Tyr | His | Phe | Trp | Tyr | QYHFWY |
| 12 | Trp | Ser | Ser | Lys | Arg | Tyr | WSSKRY |
| 13 | Trp | Ile | Lys | Trp | Thr | Lys | WIKWTK |
| 14 | Arg | Arg | Lys | Tyr | Leu | Trp | RRKYLW |
| 15 | Arg | Leu | Trp | Arg | Tyr | Gly | RLWRYG |
| 16 | Asn | Trp | Lys | Arg | Val | Arg | NWKRVR |
| 17 | Ile | Trp | Arg | Lys | Tyr | Ser | IWRKYS |
| 18 | Ile | Lys | Arg | Tyr | Tyr | Asn | IKRYYN |
| 19 | IIe | Lys | Arg | Tyr | Tyr | Leu | IKRYYL |

As used herein, an available AlPI binding domain means a peptide sequence which is sterically available to bind with AlPI in the surrounding solution and which adopts a conformation that ligates AlPI with moderate to strong avidity under controlled conditions of pH, ionic strength, and solvent composition. The avidity of binding may be increased or decreased by altering the amino acids adjacent to the above listed sequences. The avidity may be modified further by altering the above mentioned conditions of solvent composition and temperature.

BRIEF DESCRIPTION OF THE FIGURES

FIG. 1 shows elution profiles (absorbance at 280 nm) of chromatographic separation on peptide VIWLVR-A-Totda- Toyopearl (SEQ ID NO:1) for injections of 5 mg hSA+a) 0 µg AlPI; b) 250 µg AlPI; c) 500 µg AlPI; and, d) 100 µg AlPI.

FIG. 2 shows the effect of point mutations of VIWLVR (SEQ ID NO: 1). The chromatographic profiles (absorbance at 280 nm) are for 1 mg AlPI in equilibration buffer (4° C.) with peptides on Ala-Totda-Toyopearl.

FIG. 3 shows the chromatographic profiles (absorbance at 280 nm) for 1 mg AlPI in equilibration buffer (4° C.) with peptides VIWLVR and VIFLVR on Ala-Totda-Toyopearl (SEQ ID 1, 37).

SPECIFIC EMBODIMENTS

Materials

Human AlPI, human serum albumin, and Effluent I+III were manufactured by the Bayer Corporation (Clayton, N.C.). Casein (Blocker™ casein 1%(w/v) in phosphate buffered saline) was from Pierce (Rockford, Ill.). Fmoc amino acids were from Novobiochem. $^{14}$C-labeled formaldehyde was from Dupont-NEN (Boston, Mass.). Agarose was from Biorad (Hercules, Calif.). All other chemicals were reagent grade or better.

General Methods

Peptides and a 6-mer combinatorial library were synthesized on Toyopearl AF Chelate 650 M (Tosohaas, Montgomeryville, Pa.) modified with 4,7,10-trioxa- 1,13-tridecanediamine (Totda; Aldrich, St. Louis, Mo.), using standard Fmoc chemistry as described in Buettner et al. (1996). Peptides were synthesized robotically with a Gilson AMS 422. Peptide densities in the library were typically in the range of 0.2–0.5 mmole/g resin. Alpha-1-proteinase inhibitor binding peptides were isolated and identified using a modified version of a radiological screening technique (Kassarjian et al., 1993; Turck, 1994; Mondorf et al., 1997).

Peptides were re-synthesized directly onto the Toyopearl 650 Chelate resin which had been modified with Totda followed by an alanine residue, at a final substitution density of 0.1 mmole/g resin. This peptide density is lower than the peptide density for the peptide library. To control the lower peptide density, a mixture of 1:10 of Fmoc-L-Alanine to tBoc-L-Alanine was used as described in Buettner et al. (1997). Unless otherwise stated all peptide resins have a peptide density of approximately 0.1 mmol peptide/g resin. When the peptide density was altered, the ratio of Fmoc-L-Alanine to tBoc-L-Alanine was reduced. The subsequent peptide synthesis was performed maintaining a 5–10 fold excess of amino acid derivative to available Fmoc-L-Alanine residues.

Analytical Methods

Immunonephelometry was performed on two different machines. The first was a Behring Nephelometer, model BNA, with assay kits purchased from Behringwerke AG (Marburg, DEU). The second was the Beckman Array 360CE, with assay kits purchased from Beckman Instruments (Brea, Calif.).

The activity of AlPI was measured using its elastase inhibitory capacity, using a chromogenic substrate for elastase. Hydrolysis of N-succinyl-L-alanyl-L-alanyl-L-alanyl-p-nitroanilide by elastase causes an increase in absorption at 405 nm. The increase is continuously monitored. Comparisons of the linear changes of absorbance with time in the presence and absence of sample are made. The amount of inhibitor is calculated based on a calibration with known standards of AlPI and based on the 1:1 stoichiometric relationship between AlPI and elastase.

Peptide densities were determined by quantitative amino acid analysis performed at Commonwealth Biotechnologies, Inc., Richmond, Va., using a Hewlett Packard Amino Quant Chemistry system. Peptide sequences from library beads were determined by Edman degradation at the Protein Chemistry Laboratory at Texas A&M University.

Discovery of Peptides Which Bind To AlPI

An assay similar to the one used described by Mondorf (Mondorf et al., 1997) was used to deduce peptides that bind AlPI. A 6-mer combinatorial peptide library was synthesized directly onto a TosoHaas chromatography resin, Toyopearl 650M Chelate, which was modified by amination with Totda to a substitution density of approximately 0.2–0.5 mmole/g resin. The library was synthesized using Fmoc chemistry with 18 of the 20 natural amino acids (excepting cysteine and methionine).

Sequence identification utilized a radiological detection approach. AlPI was labeled at 25° C. with $^{14}$C by reductive methylation utilizing sodium cyanoborohydride and $^{14}$C-formaldehyde as described by Jentoft et al. (1983). The labeling resulted in a radioactive yield of $9 \times 10^{14}$ DPM/mole AlPI.

Two equal aliquots of 200 mg of library beads (dry weight) were placed in separate reaction vessels (Gilson, Middleton, Wis.), washed four times each with 2 ml of 20% methanol in water, and washed again with equilibration buffer, 10 mM Hepes, 0.1 M NaCl, 0.1 v/v Tween 20, pH7. To prevent nonspecific interactions between peptide and $^{14}$C-AlPI, the library beads were first incubated with 1 ml of blocking solution, a 1:1 mixture of equilibration buffer and casein (Blocker™ Casein in PBS) for 2 hours on a rotating plate. The $^{14}$C-AlPI (20 µg) was then directly added to the bead/blocking solution slurry to a final concentration of 0.5 µM and rotated for 1.5 hours.

After completion of blocking and binding, the beads were rinsed in the reaction columns using 30 ml of equilibration buffer. After rinsing, the beads from each vessel were aliquotted equally into 4 containers. A 30 ml volume of low-melting agarose solution (2% by weight) was added to each vessel, and the slurry poured onto an 8×10″ sheet of Gelbond (FMC, Rockland, Me.). To minimize the loss of beads, the tube was rinsed a second time with agarose gel, and this gel was also plated out. The agarose gel was air-dried and exposed to a photographic film (Hyperfilm-βmax, Amersham Life Science, Arlington Heights, Ill.). After 3 days exposure at −70° C., the film was developed. The background level was extremely low with approximately 20 total signals observed from all the films. Re-exposure of the gels for an additional 7 days at −70° C. resulted in the confirmation of 19 signals. Careful alignment of the film and agarose gel allowed for identification of positive beads which were isolated. From the 19 signals, 21 beads were excised and sequenced by Edman degradation.

Of the 21 sequences, 19 are listed in Table 1. Several consistencies are noted in the returned sequences. There are three types of residues found in all the sequences: 1) positively-charged residues (Arg, His, Lys); 2) aromatic residues (Tyr, Phe, Trp); and, 3) hydrophobic, aliphatic residues (Ile, Leu, Val).

Binding Confirmation

Confirmatory binding assays were performed in a column chromatographic format on a microbore HPLC using individual peptide sequences synthesized directly onto the Toyopearl 650 M Chelate resin which had been modified with Totda followed by an alanine residue (A-Totda-Toyopearl), at a final substitution density of 0.1 mmole/g resin. The resin was packed into 0.4×5 cm columns (Thomson, Springfield, Va.) and tested on the Michrom HPLC system (Michrom BioResources, Auburn, Calif.). The elution program for all trials utilized the following method. The column was pre-equilibrated with equilibration buffer (as above). 1 ml of sample was injected and allowed sufficient time to flowthrough the column using equilibration buffer. The column was then washed with step elutions of 1M NaCl and 3M NaCl in equilibration buffer. The column was exposed to equilibration buffer with 0.1M NaCl. Any remaining protein was eluted with elution buffer (2% by volume glacial acetic acid in water).

A Gilson FC204 fraction collector at the HPLC outlet collected individual eluates for further analysis. Fractions collected from the 2% acetic acid eluates were neutralized with 2M Tris, pH 10.5 to bring the pH to neutrality. The protein samples were reconstituted in equilibration buffer unless otherwise stated. The samples were analyzed by the integration of the absorbance at 280 nm or by immunonephelometry. The specific method of determination is presented for each figure.

Results

Tables 2 and 3 present the elution profiles for 19 sequences based on the injection of 1 mg A1PI in equilibration buffer at 4° C. and 20° C., respectively. The columns were run at a constant flow rate of 865 μl/min (413 cm/hr) or 523 μl/min (250 cm/hr). No dependence of the elution profile with flow rate was found. The Percent A1PI Eluted by Fraction represents the amount eluted in the flowthrough, 1M NaCl wash, and 2% acetic acid fractions relative to the total A1PI eluted. The percentages are based on either the integration of the peak areas at

TABLE 2

A1PI Binding at 4° C.
Percent A1PI eluted based on the integration of absorbance peaks at 280 nm. Results based on the injection of 1 mg A1PI in equilibration buffer at 4° C. The injections were run at a constant flow rate of 523 μl/min (250 cm/hr). Percent Eluted by Fraction represents amount of A1PI eluted in each fraction relative to the total.

| SEQ ID | Peptide Sequence | Percent A1PI Eluted by Fraction Based on Absorbance at 280 nm | | |
|---|---|---|---|---|
| | | Flowthrough | 1M NaCl | 2% Acetic Acid |
| 1 | VIWLVR | 45 | 25 | 30 |
| 2 | IIWLYK | 0 | 52 | 48 |
| 3 | RYRIFI | 0 | 40 | 60 |
| 4 | RAFWYI | 0 | 55 | 45 |
| 5 | RFIYYT | 0 | 57 | 43 |
| 6 | YKFRFW | 0 | 64 | 36 |
| 7 | LIVHRW | 0 | 74 | 26 |
| 8 | PYWIVR | 0 | 74 | 26 |
| 9 | WKLWRW | 0 | 80 | 20 |
| 10 | ARWYIH | 0 | 55 | 45 |
| 11 | QYHFWY | 0 | 74 | 26 |
| 12 | WSSKRY | 0 | 91 | 9 |
| 13 | WIKWTK | 0 | 100 | 0 |
| 14 | RRKYLW | 0 | 92 | 8 |
| 15 | RLWRYG | 0 | 88 | 12 |
| 16 | NWKRVR | 0 | 95 | 5 |

TABLE 2-continued

A1PI Binding at 4° C.
Percent A1PI eluted based on the integration of absorbance peaks at 280 nm. Results based on the injection of 1 mg A1PI in equilibration buffer at 4° C. The injections were run at a constant flow rate of 523 μl/min (250 cm/hr). Percent Eluted by Fraction represents amount of A1PI eluted in each fraction relative to the total.

| SEQ ID | Peptide Sequence | Percent A1PI Eluted by Fraction Based on Absorbance at 280 nm | | |
|---|---|---|---|---|
| | | Flowthrough | 1M NaCl | 2% Acetic Acid |
| 17 | IWRKYS | 0 | 94 | 6 |
| 18 | IKRYYN | 0 | 100 | 0 |
| 19 | IKRYYL | 0 | 97 | 3 |

280 nm or a mass balance based on immunonephelometry. Comparison of the two methods of quantitation yielded differences less than 15%.

Peptides denoted sequence ID numbers 1–19 showed capture of all or the majority of the A1PI loaded at 4° C. At 20° C., all but sequence number 11 showed the ability to bind A1PI under the given conditions. The binding strength of the peptides varied as some showed capture with complete elution in 1M NaCl, while others showed two modes of binding with A1PI eluting in both 1M NaCl and 2% acetic acid.

TABLE 3

A1PI Binding at 20° C.
Percent A1PI eluted based on the integration of absorbance peaks at 280 nm or mass balance calculated by immunonephelometry. Results based on the injection of 1 mg A1PI in equilibration buffer at 20° C. The injections were run at a constant flow rate of 523 μl/min (250 cm/hr). Percent Eluted by Fraction represents amount of A1PI eluted in each fraction relative to the total.

| SEQ ID | Peptide Sequence | Percent A1PI Eluted by Fraction | | |
|---|---|---|---|---|
| | | Flowthrough | 1M NaCl | 2% Acetic Acid |
| 1 | VIWLVR | 8 | 26 | 66 |
| 2 | IIWLYK | 28 | 17 | 55 |
| 3 | RYRIFI | 0 | 35 | 65 |
| 4 | RAFWYI | 0 | 72 | 28 |
| 5 | RFIYYT | 0 | 64 | 36 |
| 6 | YKFRFW | 0 | 75 | 25 |
| 7 | LIVHRW | 0 | 64 | 36 |
| 8 | PYWIVR | 0 | 55 | 45 |
| 9 | WKLWRW | 0 | 67 | 33 |
| 10 | ARWYIH | 0 | 84 | 16 |
| 11 | QYHFWY | 96 | 0 | 4 |
| 12 | WSSKRY | 0 | 97 | 3 |
| 13 | WIKWTK | 7 | 91 | 2 |
| 14 | RRKYLW | 0 | 82 | 18 |
| 15 | RLWRYG | 0 | 88 | 12 |
| 16 | NWKRVR | 0 | 93 | 7 |
| 17 | IWRKYS | 0 | 81 | 19 |
| 18 | IKRYYN | 0 | 95 | 5 |
| 19 | IKRYYL | 0 | 92 | 8 |

Columns were assayed with a mixture of 5 mg human serum albumin (hSA)+1 mg A1PI at 4° C. (Table 4, Seq. ID 1–11, 15, 17) and 20° C. (Table 5, Seq. ID 1–10, 13, 15, 17). The chromatography method was modified to provide for a 10 minute residence time of sample in the column by decreasing the flow to 17 μl/min (10 cm/hr) upon injection. Following the incubation, the flow was set at 865 μl/min (413 cm/hr) for the step elutions of 1M NaCl, 3M NaCl, and 2% acetic acid. The mass balances presented are based upon immunonephelometry. The Percent Eluted value is protein-specific and based on the amount of the protein eluted in a

TABLE 4

A1PI Purification at 4° C.
Mass balance for columns based on the injection of 5 mg hSA + 1 mg A1PI
at 4° C. The masses are based on immunonephelometry. Percent Eluted
by Fraction values in parentheses are protein-specific and represent the amount
of the given protein eluted in the fraction relative to the total eluted.

| SEQ ID | Peptide Sequence | Protein | Mass Protein per Eluate Fraction, mg (Percent Eluted by Fraction) | | | |
|---|---|---|---|---|---|---|
| | | | Flow | 1M NaCl | 3M NaCl | 2% Ac. Acid |
| 1 | VIWLVR | A1PI | 0.29 (38) | 0.20 (26) | 0.01 (1) | 0.27 (35) |
| | | hSA | 3.35 (67) | 1.61 (32) | * (0) | 0.04 (1) |
| 2 | IIWLYK | A1PI | 0.52 (65) | 0.10 (13) | * (0) | 0.18 (23) |
| | | hSA | 3.43 (74) | 1.17 (25) | * (0) | 0.04 (1) |
| 3 | RYRIFI | A1PI | * (0) | 0.27 (28) | * (0) | 0.71 (72) |
| | | hSA | * (0) | 4.69 (98) | 0.10 (2) | * (0) |
| 4 | RAFWYI | A1PI | 0.26 (29) | 0.19 (21) | * (0) | 0.45 (50) |
| | | hSA | 1.71 (37) | 2.93 (63) | * (0) | 0.02 (0) |
| 5 | RFIYYT | A1PI | 0.03 (3) | 0.27 (27) | 0.04 (4) | 0.64 (66) |
| | | hSA | 0.11 (2) | 4.98 (94) | * (0) | 0.18 (3) |
| 6 | YKFRFW | A1PI | * (0) | 0.28 (36) | 0.04 (5) | 0.46 (60) |
| | | hSA | * (0) | 4.14 (100) | * (0) | 0.00 (0) |
| 7 | LIVHRW | A1PI | * (0) | 0.40 (62) | * (0) | 0.24 (38) |
| | | hSA | 0.53 (12) | 4.02 (88) | * (0) | * (0) |
| 8 | PYWIVR | A1PI | 0.19 (27) | 0.31 (44) | 0.02 (3) | 0.19 (27) |
| | | hSA | 1.26 (30) | 2.93 (70) | * (0) | * (0) |
| 9 | WKLWRW | A1PI | 0.17 (25) | 0.44 (66) | * | 0.06 (9) |
| | | hSA | 0.43 (10) | 3.86 (90) | * | * (0) |
| 10 | ARWYIH | A1PI | * (0) | 0.33 (43) | 0.04 (5) | 0.41 (53) |
| | | hSA | * (0) | 4.13 (97) | 0.15 (3) | * (0) |
| 11 | QYHFWY | A1PI | 0.06 (7) | 0.35 (46) | * (0) | 0.35 (46) |
| | | hSA | 0.93 (20) | 3.76 (80) | * (0) | * (0) |
| 15 | RLWRYG | A1PI | 0.01 (2) | 0.50 (80) | * (0) | 0.11 (18) |
| | | hSA | 0.04 (1) | 4.17 (91) | 0.35 (8) | * (0) |
| 17 | IWRKYS | A1PI | 0.03 (4) | 0.68 (96) | * (0) | * (0) |
| | | hSA | 0.15 (3) | 4.67 (97) | * (0) | * (0) |

* Below detection limit

TABLE 5

A1PI Purification at 20° C.
Mass balance for columns based on the injection of 5 mg hSA + 1 mg A1PI at 20° C.
The masses are based on immunonephelometry. Percent Eluted by Fraction values in
parentheses are protein-specific and represent the amount of the given
protein eluted in the fraction relative to the total eluted.

| SEQ ID | Peptide Sequence | Protein | Mass Protein per Eluate Fraction, mg (Percent Eluted by Fraction) | | | |
|---|---|---|---|---|---|---|
| | | | Flow | 1M NaCl | 3M NaCl | 2% Ac. Acid |
| 1 | VIWLVR | A1PI | 0.08 (9) | 0.08 (9) | 0.02 (2) | 0.65 (80) |
| | | hSA | 1.90 (46) | 2.23 (54) | 0.00 (0) | 0.00 (0) |
| 2 | IIWLYK | A1PI | 0.26 (33) | 0.07 (9) | * (0) | 0.47 (58) |
| | | hSA | 5.06 (88) | 0.68 (12) | * (0) | 0.04 (1) |
| 3 | RYRIFI | A1PI | 0.22 (24) | 0.21 (23) | * (0) | 0.50 (53) |
| | | hSA | 0.78 (16) | 4.17 (84) | * (0) | 0.03 (1) |
| 4 | RAFWYI | A1PI | 0.09 (11) | 0.14 (19) | * (0) | 0.54 (70) |
| | | hSA | 0.31 (6) | 5.15 (94) | * (0) | 0.04 (1) |
| 5 | RFIYYT | A1PI | 0.29 (35) | 0.11 (12) | * (0) | 0.44 (53) |
| | | hSA | 3.07 (64) | 1.68 (35) | * (0) | 0.03 (1) |
| 6 | YKFRFW | A1PI | 0.41 (48) | 0.16 (18) | * (0) | 0.30 (34) |
| | | hSA | 1.10 (23) | 3.76 (77) | * (0) | 0.04 (1) |
| 7 | LIVHRW | A1PI | 0.34 (39) | 0.15 (18) | * (0) | 0.37 (43) |
| | | hSA | 1.39 (31) | 3.00 (68) | * (0) | 0.04 (1) |
| 8 | PYWIVR | A1PI | 0.07 (9) | 0.32 (41) | 0.02 (2) | 0.38 (48) |
| | | hSA | 0.58 (13) | 3.89 (87) | * (0) | * (0) |
| 9 | WKLWRW | A1PI | 0.16 (21) | 0.15 (20) | 0.05 (7) | 0.40 (52) |
| | | hSA | 0.25 (7) | 3.37 (93) | 0.00 (0) | 0.00 (0) |
| 10 | ARWYIH | A1PI | 0.67 (69) | 0.16 (16) | * (0) | 0.15 (15) |
| | | hSA | 2.50 (53) | 2.18 (46) | * (0) | 0.04 (1) |

TABLE 5-continued

A1PI Purification at 20° C.
Mass balance for columns based on the injection of 5 mg hSA + 1 mg A1PI at 20° C.
The masses are based on immunonephelometry. Percent Eluted by Fraction values in
parentheses are protein-specific and represent the amount of the given
protein eluted in the fraction relative to the total eluted.

| SEQ ID | Peptide Sequence | Protein | Mass Protein per Eluate Fraction, mg (Percent Eluted by Fraction) | | | |
|---|---|---|---|---|---|---|
| | | | Flow | 1M NaCl | 3M NaCl | 2% Ac. Acid |
| 13 | WIKWTK | A1PI | 0.02 (3) | 0.80 (97) | * (0) | * (0) |
| | | hSA | 0.13 (3) | 3.70 (97) | * (0) | * (0) |
| 15 | RLWRYG | A1PI | * (0) | 0.42 (48) | 0.00 (0) | 0.45 (52) |
| | | hSA | * (0) | 4.54 (98) | 0.10 (2) | 0.00 (0) |
| 17 | IWRKYS | A1PI | * (0) | 0.58 (83) | 0.00 (0) | 0.11 (17) |
| | | hSA | * (0) | 4.45 (99) | 0.05 (1) | 0.00 (0) |

* Below detection limit fraction relative to the total mass of the protein eluted. As seen in the tables, many of the columns captured hSA in addition to Al PI, but eluted the majority of hSA in the 1 M NaCl wash. Therefore, purification of AlPI from hSA was observed in the 2% acetic acid fractions which were highly enriched in AlPI relative to hSA. The AlPI present in these 2% acetic acid fractions ranged from 25–80% of the total AlPI loaded for some of the peptide ligands.

At 4° C., peptide sequences 1–11 and 15 displayed the ability to purify AlPI from hSA. At 20° C., peptide sequences 1–10, 15, and 17 were able to purify AlPI from hSA. Sequences for which data is not presented in Tables 4 and 5 showed results similar to sequence 17 at 4° C. in which both AlPI and hSA were bound and eluted in 1M NaCl. No separation between the two proteins was observed.

In experiments conducted at 20° C., AlPI at increasing masses of 250, 500, and 1000 μg AlPI in 5 mg hSA was injected into the column. The increasing capture and elution of AlPI in the acetic acid eluate was observed in the absorbance traces presented in FIG. 1 for Val-Ile-Trp-Leu-Val-Arg (SEQ ID 1). The overlaid chromatograms reveal an increase in acetic acid eluate peak area with increasing AlPI concentration. The absorbance increase for the acid eluates was confirmed as AlPI by nephelometry. The mass of AlPI eluted in the acid eluate for the successive injections of 250, 500, and 1000 μg is presented in Table 6 for SEQ ID NO's 4, 8, and 10. No hSA was detected in these fractions.

TABLE 6

Acid Eluate Yields of AlPI at 20° C.

The mass of AlPI eluted in the acid eluate fraction (based on nephelometry) for the injection of 5 mg hSA + 250, 500, and 1000 μg AlPI at 20° C. No hSA was detected in any of these fractions.

| Peptide Sequence | SEQ ID | Mass AlPI Eluted in Acid Eluate, mg Mass AlPI injected with 5 mghSA | | |
|---|---|---|---|---|
| | | 250 μg | 500 μg | 1000 μg |
| PYWIVR | 4 | 0.09 | 0.21 | 0.30 |
| RLWRYG | 8 | 0.07 | 0.15 | 0.39 |
| VIWLVR | 10 | 0.18 | 0.48 | 0.70 |

EXAMPLE 1

Purification from Effluent II+III

Sequences 1–11 and 15 were assayed with Effluent II+III (Eff. II+III). Eff. II+III is a process intermediate in the Cohn plasma fractionation process. The feed stream contains 20% (by volume) ethanol, 20–25 mg/ml hSA and approximately 1 mg/ml AlPI. The stream also contains other proteins including anti-thrombin III (AT3), immunoglobin G (IgG), immunoglobin A (IgA), apolipoprotein alpha-1 (Apo A-1), transferrin (Trf), haptoglobin (Hpt), and alpha-1 acid glycoprotein (AAG) at concentrations ranging from 0.1–1 mg/ml.

The columns were assayed using the same technique as the hSA+AlPI experiments, allowing for a 10 minute residence time followed by a constant flow rate of 865 μl/min with step elutions of 1M NaCl, 3M NaCl, and 2% acetic acid. All experiments were conducted at 4° C. The mass balances for the injection of 1 ml Eff. II+III are presented in Table 7. The majority of sequences tested (ID 1–6, 10–11) showed capture of greater than 50% of the AlPI loaded on the column with significant purification of AlPI in the acid eluate. The AlPI was enriched from 3% of the total protein in the feed to upwards of 50% in the acid eluate.

TABLE 7

Purification of A1PI from Effluent II + III
These tables present the mass balance of proteins from the injection of
1 ml Eff. II + III into a 0.6 ml column at 4° C.. The values are based on
immunonephelometry. Mass balances for alpha-1 acid glycoprotein,
haptoglobin, and transferrin are not presented as these proteins were
detected in the flowthrough only for all sequences, except for
Haptoglobin-LIVHRW (SEQ ID 7) (data presented). Data presented for
apolipoprotein alpha-1 (Apo A-1), Immunoglobulin A (IgA), and
Immunoglobulin G (IgG).

| Protein | Mass Protein per Eluate Fraction, mg (Percent Eluted by Fraction) | | | |
|---|---|---|---|---|
| | Flow | 1M NaCl | 3M NaCl | 2% Acetic Acid |
| VIWLVR: [SEQ ID NO: 1] | | | | |
| A1PI | 0.58 (48) | 0.10 (9) | * (0) | 0.51 (43) |
| hSA | 26.64 (97) | 0.69 (3) | * (0) | * (0) |
| Apo A-1 | 0.32 (52) | * (0) | * (0) | 0.29 (48) |
| IgA | 0.17 (37) | 0.11 (24) | * (0) | 0.18 (39) |
| IgG | 0.36 (94) | 0.02 (6) | * (0) | * (0) |
| IIWLYK: [SEQ ID NO: 2] | | | | |
| A1PI | 0.13 (21) | * (0) | * (0) | 0.50 (79) |
| hSA | 14.93 (78) | 4.10 (21) | 0.11 (1) | 0.12 (1) |
| Apo A-1 | * (0) | * (0) | * (0) | 0.43 (100) |
| IgA | 0.06 (17) | 0.12 (34) | * (0) | 0.17 (49) |
| IgG | 0.23 (91) | 0.02 (9) | * (0) | * (0) |
| RYRIFI: [SEQ ID NO: 3] | | | | |
| A1PI | 0.19 (25) | 0.07 (9) | * (0) | 0.50 (66) |
| hSA | 9.35 (48) | 9.93 (51) | 0.12 (1) | * (0) |

TABLE 7-continued

Purification of A1PI from Effluent II + III
These tables present the mass balance of proteins from the injection of 1 ml Eff. II + III into a 0.6 ml column at 4° C.. The values are based on immunonephelometry. Mass balances for alpha-1 acid glycoprotein, haptoglobin, and transferrin are not presented as these proteins were detected in the flowthrough only for all sequences, except for Haptoglobin-LIVHRW (SEQ ID 7) (data presented). Data presented for apolipoprotein alpha-1 (Apo A-1), Immunoglobulin A (IgA), and Immunoglobulin G (IgG).

Mass Protein per Eluate Fraction, mg
(Percent Eluted by Fraction)

| Protein | Flow | 1M NaCl | 3M NaCl | 2% Acetic Acid |
|---|---|---|---|---|
| Apo A-1 | * (0) | * (0) | * (0) | 0.39 (100) |
| IgA | 0.08 (22) | 0.06 (17) | * (0) | 0.23 (60) |
| IgG | 0.24 (100) | * (0) | * (0) | * (0) |
| RAFWYI: [SEQ ID NO: 4] | | | | |
| A1PI | 0.18 (17) | 0.04 (4) | * (0) | 0.87 (80) |
| hSA | 9.67 (49) | 9.80 (50) | 0.11 (1) | * (0) |
| Apo A-1 | * (0) | * (0) | * (0) | 0.29 (100) |
| IgA | 0.12 (35) | 0.12 (36) | * (0) | 0.10 (29) |
| IgG | 0.24 (91) | 0.02 (9) | * (0) | * (0) |
| RFIYYT: [SEQ ID NO: 5] | | | | |
| A1PI | 0.15 (15) | 0.05 (5) | * (0) | 0.81 (80) |
| hSA | 9.32 (47) | 10.25 (52) | 0.11 (1) | * (0) |
| Apo A-1 | * (0) | * (0) | * (0) | 0.37 (100) |
| IgA | 0.10 (31) | 0.10 (31) | * (0) | 0.12 (38) |
| IgG | 0.23 (86) | 0.02 (7) | * (0) | 0.02 (7) |
| YKFRFW: [SEQ ID NO: 6] | | | | |
| A1PI | 0.16 (14) | 0.06 (5) | * (0) | 0.92 (81) |
| hSA | 9.35 (49) | 9.45 (50) | 0.20 (1) | * (0) |
| Apo A-1 | * (0) | * (0) | * (0) | 0.31 (100) |
| IgA | 0.13 (37) | 0.11 (33) | * (0) | 0.10 (30) |
| LIVHRW: [SEQ ID NO: 7] | | | | |
| A1PI | 0.71 (59) | 0.20 (16) | * (0) | 0.30 (25) |
| hSA | 15.13 (68) | 7.23 (32) | * (0) | * (0) |
| Apo A-1 | 0.28 (49) | * (0) | * (0) | 0.30 (51) |
| IgA | 0.15 (37) | 0.18 (43) | * (0) | 0.08 (20) |
| IgG | 0.31 (100) | * (0) | * (0) | * (0) |
| Hpt | 0.43 (60) | 0.29 (40) | * (0) | * (0) |
| PYWIVR: [SEQ ID NO: 8] | | | | |
| A1PI | 0.55 (56) | 0.15 (16) | * (0) | 0.28 (29) |
| hSA | 20.58 (89) | 2.64 (11) | * (0) | * (0) |
| Apo A-1 | 0.22 (40) | 0.34 (60) | * (0) | * (0) |
| IgA | 0.08 (21) | 0.22 (57) | * (0) | 0.08 (22) |
| IgG | 0.30 (90) | 0.03 (10) | * (0) | * (0) |
| ARWYIH: [SEQ ID NO: 10] | | | | |
| A1PI | 0.20 (18) | 0.08 (7) | * (0) | 0.81 (75) |
| hSA | 9.98 (53) | 8.64 (46) | 0.25 (1) | * (0) |
| Apo A-1 | * (0) | * (0) | * (0) | 0.29 (100) |
| IgA | 0.09 (25) | 0.07 (18) | * (0) | 0.21 (56) |
| IgG | 0.23 (93) | * (0) | * (0) | 0.02 (7) |
| QYHFWY: [SEQ ID NO: 11] | | | | |
| A1PI | 0.21 (20) | 0.06 (6) | * (0) | 0.80 (75) |
| hSA | 13.26 (75) | 4.38 (25) | * (0) | 0.11 (1) |
| Apo A-1 | * (0) | * (0) | * (0) | * (0) |
| IgA | 0.11 (31) | 0.11 (31) | * (0) | 0.13 (38) |
| IgG | 0.21 (90) | 0.02 (10) | * (0) | * (0) |
| RLWRYG: [SEQ ID NO: 15] | | | | |
| A1PI | 0.59 (64) | 0.20 (22) | * (0) | 0.13 (14) |
| hSA | 8.78 (43) | 11.18 (54) | 0.69 (3) | * (0) |
| Apo A-1 | * (0) | * (0) | * (0) | 0.35 (100) |
| IgA | 0.19 (69) | * (0) | * (0) | 0.09 (31) |
| IgG | 0.27 (100) | * (0) | * (0) | * (0) |

EXAMPLE 2

Further Characterization of Binding Sequence VIWLVR (SEQ ID NO:1)

Point mutations of the sequence VIWLVR (SEQ ID NO:1) were undertaken to understand the importance of various residues in binding A1PI. These experiments were conducted at a constant flow rate of 523 μl/min (250 cm/hr) by injecting 1 mg A1PI in equilibration buffer. After loading and flowthrough with equilibration buffer, the column was subjected to step elutions of 1M and 3M NaCl and 2% acetic acid. The results, based on the absorbance at 280 nm, are presented in Table 8 (4° C. only) and Table 9 (4 and 20° C.).

The replacement of the two residues at the N-terminus, the hydrophobic Val and Ile, with the hydrophilic residues Asp, His, Asn, and Ser revealed important considerations for A1PI capture and binding strength. FIG. 2 presents the chromatograms for sequences DDWLVR, SNWLVR, and VIWLVR (SEQ ID NO: 21, 28, 1) and shows the shift in the capture and elution behavior as a result of sequence modification. Placement of the negatively charged Asp in either of the two positions largely prevented binding, highlighting the importance of a N-terminal positive charge for binding (Table 8a). The only sequences which showed appreciable capture of A1PI in the presence of the Asp residue are those which contained His, a positively-charged residue. Non-Asp containing sequences were shown to

TABLE 8

A1PI Binding by VIWLVR (SEQ ID NO: 1) Point Mutations
Assessment of the effect of the residues Asn, His, Asp, and Ser at the two N-terminal positions on A1PI capture and elution. Results based on the injection of 1 mg A1PI in equilibration buffer at 4° C. The injections were run at a constant flow rate of 523 μl/min (250 cm/hr). Percent Eluted by Fraction represents amount of A1PI eluted in each fraction relative to the total as determined by integration of the absorbance at 280 nm.

| SEQ ID NOS. | Peptide Sequence | % of Total A1PI Eluted by Fraction (Based on Absorbance at 280 nm) | | |
|---|---|---|---|---|
| | | Flowthrough | 1M NaCl | 2% Acetic Acid |
| (a) - Effect of negative charge on binding at 4° C. | | | | |
| 1 | VIWLVR | 45 | 25 | 30 |
| 20 | SDWLVR | 98 | 1 | 1 |
| 21 | DDWLVR | 99 | 0 | 1 |
| 22 | NDWLVR | 100 | 0 | 0 |
| 23 | DSWLVR | 90 | 10 | 0 |
| 24 | DNWLVR | 90 | 9 | 1 |
| 25 | DHWLVR | 53 | 37 | 10 |
| 26 | HDWLVR | 70 | 30 | 0 |
| (b) - Effect of hydrophilic residues on binding at 4° C. | | | | |
| 1 | VIWLVR | 45 | 25 | 30 |
| 27 | SSWLVR | 0 | 94 | 6 |
| 28 | SNWLVR | 0 | 95 | 5 |
| 29 | SHWLVR | 0 | 87 | 13 |
| 30 | HSWLVR | 0 | 89 | 11 |
| 31 | HNWLVR | 0 | 92 | 8 |
| 32 | HHWLVR | 0 | 86 | 14 |
| 33 | NHWLVR | 0 | 83 | 17 |
| 34 | NSWLVR | 52 | 43 | 5 |
| 35 | NNWLVR | 83 | 13 | 4 | exhibit similar capture as Val-Ile-Trp-Leu-Val-Arg (SEQ ID NO:1), but with a significant change in interaction strength as the majority of the A1PI eluted in 1M NaCl (Table 8b). Therefore, the two residues at the N-terminal require a positive charge and a hydrophobic character for capture and purification.

The importance of the aromatic residue Trp at position 3 was investigated by residue substitution and testing at 4 and 20° C. (Table 9). A1PI capture and interaction strength increased with replacement by the aromatic residues Tyr and Phe, hydrophobic Val and Leu, and the polar Asn. One hundred percent of the A1PI was captured by these sequences with 72–97% of the total A1PI eluting in 2% acetic acid. FIG. 3 shows a comparison of sequences VIWLVR and VIFLVR (SEQ ID NO:1 and 37) for the injection of A1PI at 4° C. As seen earlier, the introduction of a negative charge (Asp) prevented any binding of A1PI. The substitution of the hydroxyl-containing Ser, less hydrophobic Ala, or positively-charged Arg did not affect A1PI capture, but resulted in the elution of A1PI in both the 1M NaCl and 2% acetic acid eluates at 20° C. and almost exclusively in 1M NaCl at 4° C.

Table 10 shows the increased yield of purified A1PI for sequences VIWLVR (SEQ ID NO:36) and VIFLVR (SEQ ID NO:37) relative to VIWLVR (SEQ ID NO:1) for the injection of 5 mg hSA+1 mg A1PI in equilibration buffer at 4° C. and 20° C. The sequences with higher A1PI yields in the acid eluates under aqueous conditions also provided superior yields of A1PI from Eff. II+III (Table 11) compared to VIWLVR (SEQ ID NO:1). The yield of A1PI in the acid eluate increased for many of the point mutations while the elution characteristics of the other proteins in Eff. II+III were largely unaffected, providing similar performance to VIWLVR (SEQ ID NO:1). The sequence VIFLVR (SEQ ID NO:37) exhibited the best performance for both the aqueous and Eff. II+III feeds.

TABLE 9

A1PI Binding by VIWLVR (SEQ ID NO: 1) Point Mutations
Assessment of the importance of the Trp residue on A1PI capture and elution. Results based on the injection of 1 mg A1PI in equilibration buffer at (a) 4° C. and (b) 20° C.. The injections were run at a constant flow rate of 523 μl/min (250 cm/hr). Percent Eluted by Fraction represents amount of A1PI eluted in each fraction relative to the total as determined by integration of the absorbance at 280 nm or immunonephelometry.

| SEQ ID NOS. | Peptide Sequence | | | | | Flow-through | 1M NaCl | 2% Acetic Acid |
|---|---|---|---|---|---|---|---|---|
| | | | | | | % of Total A1PI Eluted by Fraction (Based on Absorbance at 280 nm) | | |
| (a) 4° C. | | | | | | | | |
| 1  | V | I | W | L | V | R | 45  | 25  | 30 |
| 36 | V | I | Y | L | V | R | 0   | 28  | 72 |
| 37 | V | I | F | L | V | R | 0   | 3   | 97 |
| 38 | V | I | L | L | V | R | 0   | 7   | 93 |
| 39 | V | I | V | L | V | R | 0   | 5   | 95 |
| 40 | V | I | N | L | V | R | 0   | 8   | 92 |
| 41 | V | I | D | L | V | R | 100 | 0   | 0  |
| 42 | V | I | S | L | V | R | 0   | 100 | 0  |
| 43 | V | I | A | L | V | R | 0   | 92  | 8  |
| 44 | V | I | R | L | V | R | 0   | 90  | 10 |
| (b) 20° C. | | | | | | | | |
| 1  | V | I | W | L | V | R | 8   | 26  | 66 |
| 36 | V | I | Y | L | V | R | 0   | 15  | 85 |
| 37 | V | I | F | L | V | R | 0   | 8   | 92 |
| 40 | V | I | N | L | V | R | 0   | 7   | 93 |
| 41 | V | I | D | L | V | R | 84  | 0   | 16 |
| 42 | V | I | S | L | V | R | 11  | 75  | 14 |
| 43 | V | I | A | L | V | R | 10  | 36  | 53 |
| 44 | V | I | R | L | V | R | 0   | 45  | 55 |

TABLE 10

A1PI Purification for VIWLVR SEQ ID NO: 1) Point Mutations
Mass balance for columns based on the injection of 5 mg hSA + 1 mg A1PI at 4° C. The masses are based immunonephelometry. Percent Eluted by Fraction values in parentheses are protein-specific and represent the amount of the given protein eluted in the fraction relative to the total loaded.

| SEQ ID NOS. | Peptide Sequence | Protein | Flow | 1M NaCl | 3M NaCl | 2% Acetic Acid |
|---|---|---|---|---|---|---|
| | | | Mass Protein per Eluate Fraction, mg (Percent Eluted by Fraction) | | | |
| (a) 4° C. | | | | | | |
| 1  | VIWLVR | A1PI | 0.28 (35) | 0.21 (26) | 0.03 (4) | 0.31 (38) |
|    |        | hSA  | 3.56 (71) | 1.45 (29) | * (0)    | * (0) |
| 36 | VIYLVR | A1PI | 0.12 (12) | 0.12 (12) | * (0)    | 0.75 (76) |
|    |        | hSA  | 0.77 (17) | 3.59 (78) | 0.11 (2) | 0.11 (2) |
| 37 | VIFLVR | A1PI | 0.13 (16) | 0.05 (7)  | * (0)    | 0.61 (77) |
|    |        | hSA  | 1.84 (38) | 2.87 (60) | * (0)    | 0.10 (2) |
| (b) 20° C. | | | | | | |
| 1  | VIWLVR | A1PI | 0.08 (9)  | 0.08 (9)  | 0.02 (2) | 0.65 (80) |
|    |        | hSA  | 1.90 (46) | 2.23 (54) | * (0)    | 0.00 (0) |
| 36 | VIYLVR | A1PI | 0.13 (19) | 0.07 (11) | * (0)    | 0.48 (70) |
|    |        | hSA  | 1.85 (44) | 2.34 (56) | * (0)    | 0.00 (0) |
| 37 | VIFLVR | AlPI | 0.17 (22) | 0.02 (2)  | * (0)    | 0.60 (76) |
|    |        | hSA  | 4.33 (92) | 0.25 (5)  | * (0)    | 0.11 (2) |

* Denotes Below detection limit

TABLE 11

A1PI Yield from Effluent II + III for VIWLVR (SEQ ID NO: 1) Point Mutations
These tables present the mass balance of proteins from the injection of 1 ml
Eff. II + III into a 0.6 ml column at 4° C. The values are based on
immunonephelometry.

| SEQ ID NOS. | Peptide Sequence | | | | | | Mass A1PI per Eluate Fraction, mg (Percent Eluted by Fraction) | | |
|---|---|---|---|---|---|---|---|---|---|
| | | | | | | | Flowthrough | 1M NaCl | 2% Acetic Acid |
| 1  | V | I | W | L | V | R | 0.58 (48) | 0.10 (9)  | 0.51 (43) |
| 37 | V | I | F | L | V | R | 0.13 (18) | * (0)     | 0.57 (82) |
| 36 | V | I | Y | L | V | R | 0.22 (27) | 0.05 (6)  | 0.57 (68) |
| 43 | V | I | A | L | V | R | 0.18 (31) | 0.05 (8)  | 0.35 (61) |
| 39 | V | I | V | L | V | R | 0.31 (37) | 0.04 (4)  | 0.50 (59) |
| 40 | V | I | N | L | V | R | 0.44 (45) | * (0)     | 0.53 (55) |
| 38 | V | I | L | L | V | R | 0.42 (41) | 0.07 (7)  | 0.54 (52) |
| 42 | V | I | S | L | V | R | 0.14 (25) | 0.14 (26) | 0.26 (49) |

* Denotes Below detection limit

EXAMPLE 3

Modifications of the Sequence VIFLVR (SEQ ID NO:37)

Modifications to the sequence VIFLVR (SEQ ID NO:37) were synthesized directly onto Ala-Totda-Toyopearl resin at a density of 0.1 mmol/g to identify the relative importance of each residue for binding and interaction strength with A1PI. Table 12 shows the quantification of eluates from the resins contacted in a chromatographic format with 1 mg A1PI in equilibration buffer at 4 and 20° C.

Substitutions at the N-terminal valine (Position 1) highlighted the importance of the position. Equivalent behavior to VIFLVR (SEQ ID NO:37) was achieved by substituting the N-terminal Val with Ser, Ala, and the positively-charged Lys, His, and Arg residues. Like VIWLVR (SEQ ID NO:1), the negatively-charged residue Asp at the N-terminal position prevented the majority of A1PI from binding. Acetylation of the N-terminal amino group (i.e. converting the positively-charged amino group to an uncharged amide) also prevented the majority of A1PI from binding. A hydrophilic amide (Asn) did not affect capture, but weakened the binding as evidenced by the elution of a significant portion of A1PI with 1M NaCl at 4° C. Therefore, we may conclude that a positive charge is very important at the N-terminal position.

Substitutions at the second position (Ile) revealed its importance in determining the binding strength. The positively-charged residues (Arg, His, Lys) and Ala did not affect capture, but weakened the interaction allowing for a significant portion of A1PI to be eluted with 1M NaCl. Substitution at the fourth position (Leu) with Ala did not affect capture, but caused a significant weakening of binding with approximately equal elution of A1PI in 1M NaCl and 2% acetic acid at 4° C.

TABLE 12

A1PI Binding of VIFLVR (SEQ ID NO: 37) Point Mutations
Assessment of the effect of the various residues on A1PI capture and elution. Results based on the injection of 1 mg A1PI in equilibration buffer at (a) 4° C. and (b) 20° C. The injections were run at a constant flow rate of 523 μl/min (250 cm/hr). Percent Eluted by Fraction represents amount of A1PI eluted in each fraction relative to the total based on the absorbance at 280 nm or immunonephelometry.

| SEQ ID NOS. | Position | 1 | 2 | 3 | 4 | 5 | 6 | % of Total A1PI Eluted by Fraction (Based on Absorbance at 280 nm) | | |
|---|---|---|---|---|---|---|---|---|---|---|
| | | | | | | | | Flowthrough | 1M NaCl | 2% Acetic Acid |
| | | | | | | (a) 4° C. | | | | |
| 37 |        | V    | I | F | L | V | R | 0  | 3   | 97  |
| 45 | 1: Val | K    | I | F | L | V | R | 0  | 3   | 97  |
| 46 |        | R    | I | F | L | V | R | 0  | 0   | 100 |
| 47 |        | H    | I | F | L | V | R | 0  | 3   | 97  |
| 48 |        | S    | I | F | L | V | R | 0  | 7   | 93  |
| 49 |        | A    | I | F | L | V | R | 0  | 4   | 96  |
| 50 |        | N    | I | F | L | V | R | 0  | 25  | 75  |
| 37 |        | Ac-V | I | F | L | V | R | 76 | 2   | 22  |
| 51 |        | D    | I | F | L | V | R | 84 | 6   | 10  |
| 52 | 2: Ile | V    | H | F | L | V | R | 0  | 35  | 65  |
| 53 |        | V    | R | F | L | V | R | 0  | 39  | 61  |
| 54 |        | V    | K | F | L | V | R | 0  | 66  | 34  |
| 55 |        | V    | A | F | L | V | R | 0  | 55  | 45  |
| 56 | 4: Leu | V    | I | F | A | V | R | 0  | 46  | 54  |
| 57 | 5: Val | V    | I | F | L | A | R | 0  | 25  | 75  |

TABLE 12-continued

A1PI Binding of VIFLVR (SEQ ID NO: 37) Point Mutations
Assessment of the effect of the various residues on A1PI capture and elution. Results based on the injection of 1 mg A1PI in equilibration buffer at (a) 4° C. and (b) 20° C. The injections were run at a constant flow rate of 523 µl/min (250 cm/hr). Percent Eluted by Fraction represents amount of A1PI eluted in each fraction relative to the total based on the absorbance at 280 nm or immunonephelometry.

| SEQ ID | | | | | | | | % of Total A1PI Eluted by Fraction (Based on Absorbance at 280 nm) | | |
|---|---|---|---|---|---|---|---|---|---|---|
| NOS. | Position | 1 | 2 | 3 | 4 | 5 | 6 | Flowthrough | 1M NaCl | 2% Acetic Acid |
| 58 | | V | I | F | L | F | R | 40 | 3 | 56 |
| 59 | | V | I | F | L | Y | R | 56 | 4 | 40 |
| 60 | 6: Arg | V | I | F | L | V | A | 77 | 2 | 21 |
| | | | | | | (b) 20° C. | | | | |
| 37 | | V | I | F | L | V | R | 0 | 8 | 92 |
| 45 | 1: Val | K | I | F | L | V | R | 0 | 0 | 100 |
| 47 | | H | I | F | L | V | R | 0 | 7 | 93 |
| 48 | | S | I | F | L | V | R | 13 | 6 | 81 |
| 49 | | A | I | F | L | V | R | 5 | 3 | 92 |
| 37 | | Ac-V | I | F | L | V | R | 100 | 0 | 0 |
| 51 | | D | I | F | L | V | R | 70 | 9 | 21 |
| 54 | 2: Ile | V | K | F | L | V | R | 0 | 49 | 51 |
| 55 | | V | A | F | L | V | R | 0 | 8 | 92 |
| 56 | 4: Leu | V | I | F | A | V | R | 0 | 11 | 89 |
| 57 | 5: Val | V | I | F | L | A | R | 75 | 0 | 25 |
| 59 | | V | I | F | L | Y | R | 77 | 3 | 20 |
| 60 | 6: Arg | V | I | F | L | V | A | 92 | 0 | 8 |

Substitutions at the fifth position (Val) with an aromatic residue disrupted capture, allowing capture of 50% or less. Substitution with Ala did not affect capture but caused 25% of the A1PI to elute in 1M NaCl.

The importance of the peptide's positive charge was reiterated by replacement of the C-terminal Arg with the uncharged Ala. The new sequence bound less than 20% of the A1PI loaded. Therefore, a second positive charge (in addition to the N-terminal amine) is very important for binding.

Based on the performance with pure A1PI under aqueous conditions, several of the columns were assayed using Eff. II+III. The results are presented in Table 13 and summarized for the A1PI mass balance. The table presents the mass in each fraction based on immunonephelometry and the fraction of A1PI eluted in each fraction. Substitutions with positively charged residues at the N-terminus revealed behavior similar to VIFLVR (SEQ ID NO:37), while other substitutions which appeared to work as well for aqueous conditions did not perform as well for Eff. II+III. Only those sequences with a positively-charged residue at the N-terminal position performed as well as VIFLVR (SEQ ID NO:37).

TABLE 13

A1PI Yield from Effluent II + III for VIFLVR (SEQ ID NO:37) Point Mutations
These tables present the mass balance of proteins from the injection of 1 ml Eff. II + III into a 0.6 ml column at 4° C.
The values are based on immunonephelometry.

| SEQ ID | Peptide | | | | | | Mass A1PI per Eluate Fraction, mg (Percent Eluted by Fraction) | | |
|---|---|---|---|---|---|---|---|---|---|
| NOS. | Sequence | | | | | | Flowthrough | 1M NaCl | 2% Acetic Acid |
| 37 | V | I | F | L | V | R | 0.32 (25) | 0.07 (5) | 0.91 (70) |
| 47 | H | I | F | L | V | R | 0.16 (21) | 0.08 (10) | 0.54 (69) |
| 46 | R | I | F | L | V | R | 0.24 (33) | * (0) | 0.50 (67) |
| 45 | K | I | F | L | V | R | 0.32 (38) | 0.03 (3) | 0.51 (59) |
| 49 | A | I | F | L | V | R | 0.33 (33) | 0.07 (7) | 0.59 (60) |
| 48 | S | I | F | L | V | R | 0.61 (52) | 0.04 (3) | 0.52 (44) |

* Denotes Below detection limit

EXAMPLE 4

Binding from Aqueous Effluent II+III

Effluent II+III was dialyzed against equilibration buffer at 4° C. to remove the ethanol using a 15,000 molecular weight cut-off membrane. Nephelometry of the Eff. II+III before and after dialysis revealed little protein loss to the membrane. A portion of the identified sequences were assayed under the same conditions applied for neat Eff. II+III at 4° C. Protein concentrations were determined by immunonephelometry, and the A1PI mass balances are presented in Table 14. The tested sequences exhibited decreased capture of A1PI from the dialyzed, aqueous Eff. II+III compared to the neat, ethanol-containing feed. The binding strength differed for the aqueous feed as more A1PI eluted in 1M NaCl for the aqueous feed. The A1PI eluted in the 1M NaCl fractions was not as enriched as that eluted in the acid eluates.

The reduced density columns were also tested with pure A1PI at 4° C. and 20° C. (Table 16). The aqueous based results suggest that resins at 39 μmol/g and above behave similarly with a sharp decline in the ability to capture A1PI at lower peptide densities.

TABLE 14

A1PI Yield from Dialyzed Effluent II + III
These tables present the mass balance of proteins from the injection of 1 ml Eff. II + III into a 0.6 ml column at 4° C. The values are based on immunonephelometry. The Eff. II + III was dialyzed against equilibration buffer to remove ethanol.

| SEQ ID NOS. | Peptide Sequence | | | | | Mass A1PI per Eluate Fraction, mg (Percent Eluted by Fraction) | | |
|---|---|---|---|---|---|---|---|---|
| | | | | | | Flowthrough | 1M NaCl | 2% Acetic Acid |
| 2  | I | I | W | L | V | K | 0.19 (31) | 0.05 (9)  | 0.38 (60) |
| 37 | V | I | F | L | V | R | 0.25 (36) | 0.09 (13) | 0.37 (51) |
| 3  | R | Y | R | L | F | I | 0.21 (35) | 0.15 (24) | 0.25 (41) |
| 1  | V | I | W | L | V | R | 0.24 (39) | 0.15 (24) | 0.23 (37) |
| 10 | A | R | W | Y | I | H | 0.24 (39) | 0.18 (30) | 0.20 (32) |
| 36 | V | I | Y | L | V | R | 0.46 (62) | 0.12 (16) | 0.16 (22) |

EXAMPLE 5

Effect of Peptide Density on the Binding to VIFLVR (SEQ ID No:37)

The substitution density of the peptide VIFLVR (SEQ ID NO:37) on the Tosohaas resin was reduced by the varying the ratio of Fmoc-L-Ala/Boc-L-Ala following linkage of the Totda linker. A similar procedure was outlined previously (Buettner et al. 1997). The peptide was then synthesized onto these resins. A 1.0 ml aliquot of neat Eff. II+III was injected onto the columns, and the chromatography cycle was the same as used for other studies involving Eff. II+III. The one exception was the use of 4M guanidine hydrochloride (GdnHCl) in lieu of 2% acetic acid as the final strip. The results are presented in Table 15.

TABLE 15

Effect of Peptide Density on A1PI Capture from Eff. II + III for VIFLVR (SEQ ID NO: 37)

Mass values based on immunonephelometry of collected fractions. The columns were run at 4° C. Values in parentheses represent the percent of A1PI eluted in the fraction relative to the total A1PI eluted.

| Peptide Density | Mass A1PI per Eluate Fraction, mg (Percent Eluted by Fraction) | | |
|---|---|---|---|
| (μmol/g) | Flowthrough | 1M NaCl | 4M GdnHCl |
| 100 | 0.13 (18) | * (0)     | 0.57 (82) |
| 70  | 0.26 (28) | * (0)     | 0.69 (72) |
| 62  | 0.14 (17) | * (0)     | 0.70 (83) |
| 54  | 0.20 (26) | * (0)     | 0.57 (74) |
| 17  | 0.39 (49) | 0.36 (44) | 0.05 (7)  |
| 6   | 0.69 (88) | 0.09 (12) | * (0)     |

* Denotes Below detection limit

Resins densities of 54 μmol/g and greater exhibited equivalent behavior in terms of capture and purification of A1PI from Eff. II+III. The resins at 6 and 17 μmol/g had significantly reduced capture and exhibited a decreased interaction strength between peptide-resin and bound A1PI as evidenced by the elution of A1PI in 1M NaCl rather than 4M GdnHCl.

TABLE 16

Effect of Peptide Density of VIFLVR (SEQ ID NO: 37) on A1PI Binding

Percent A1PI eluted based on the integration of absorbance peaks at 280 nm or mass balance calculated by immunonephelometry. Results based on the injection of 1 mg A1PI in equilibration buffer at 4 and 20° C. The injections were run at a constant flow rate of 523 μl/min (250 cm/hr). Percent Eluted by Fraction represents amount of A1PI eluted in each fraction relative to the total.

| Peptide Density | Percent A1PI Eluted by Fraction | | |
|---|---|---|---|
| (μmol/g) | Flowthrough | 1M NaCl | 2% Acetic Acid |
| (a) 4° C. | | | |
| 135 | 0  | 0  | 100 |
| 99  | 0  | 0  | 100 |
| 58  | 0  | 4  | 96  |
| 54  | 0  | 0  | 100 |
| 39  | 0  | 4  | 96  |
| 25  | 57 | 1  | 43  |
| 17  | 80 | 10 | 2   |
| 6   | 87 | 21 | 0   |
| (a) 20° C. | | | |
| 135 | 5  | 0  | 95  |
| 99  | 7  | 0  | 93  |
| 58  | 0  | 0  | 100 |
| 54  | 0  | 0  | 100 |
| 39  | 0  | 0  | 100 |
| 25  | 28 | 0  | 72  |
| 17  | 68 | 18 | 22  |
| 6   | 79 | 13 | 0   |

EXAMPLE 6

Effect of the N-terminal Truncation of VIFLVR (SEQ ID No:37)

The peptide sequence Val-Ile-Phe-Leu-Val-Arg (SEQ ID NO:37) was reduced sequentially from the N-terminus to identify the necessary amino acids required for binding and their effect on the binding strength. The N-terminal truncations were tested with pure A1PI at 4 and 20° C. (Table 17). Significant reduction in the capture of A1PI is observed with the removal of the N-terminal valine and diminishes further as more residues are removed. Additionally, the binding avidity changes as the captured AlPI elutes primarily or exclusively in 1M NaCl as the sequence is truncated.

TABLE 17

Effect of Sequence Truncations of VIFLR (SEQ ID NO: 37) on AlPI Binding and Elution Percent AlPI eluted based on mass balance calculated by immunonephelometry. Results based on the injection of 1 mg AlPI in equilibration buffer at 4 and 20° C. The injections were run at a constant flow rate of 523 µl/min (250 cm/hr). Percent Eluted by Fraction represents amount of AlPI eluted in each fraction relative to the total.

| | Percent AlPI Eluted by Fraction | | |
|---|---|---|---|
| Sequence | Flowthrough | 1M NaCl | 2% Acetic Acid |
| (a) 4° C. | | | |
| VIFLVR | 0 | 3 | 97 |
| IFLVR | 47 | 44 | 9 |
| FLVR | 85 | 15 | 0 |
| LVR | 70 | 30 | 0 |
| VR | 92 | 8 | 0 |
| R | 95 | 5 | 0 |
| (b) 20° C. | | | |
| VIFLVR | 0 | 7 | 93 |
| IFLVR | 29 | 47 | 24 |
| FLVR | 90 | 10 | 0 |
| LVR | 52 | 48 | 0 |
| VR | 89 | 11 | 0 |
| R | 95 | 5 | 0 |

EXAMPLE 7

Effect of Reversing Sequence VIFLVR (SEQ ID No:37)

The sequence VIFLVR (SEQ ID No:37) was reversed to assess the importance of the sequence order on binding. The sequences RVLFIV (SEQ ID No:61), RVLFIH (SEQ ID No:62), and the N-terminal acetylated Ac-RVLFIV (SEQ ID No:61) were synthesized and tested for their ability to bind pure AlPI at 4° C. and 20° C. (Table I18), while RVLFIV (SEQ ID No:61) and RVLFIH (SEQ ID No:62) were also tested with a mixture of 1 mg AlPI and 5 mg hSA (Table 19).

The reversed sequences RVLFIV (SEQ ID No:61) and RVLFIH (SEQ ID No:62) show near equivalent behavior to VIFLVR (SEQ ID No:37) at 20° C. for both pure AlPI and the purification of AlPI from a mixture with hSA. While the sequence VIFLVA (SEQ ID No:60) (Table 12), which omitted the C-terminal positive charge showed little binding of AlPI, the sequence RVLFIV (SEQ ID No:61) showed excellent binding suggesting that a

TABLE 18

Effect of Sequence Order on AlPI Binding and Elution

Percent AlPI eluted based on mass balance calculated by integration of absorbance at
280 nm or immunonephelometry. Results based on the injection of 1 mg AlPI in
equilibration buffer at 4 and 20° C. The injections were run at a constant flow rate of
523 µl/min (250 cm/hr). Percent Eluted by Fraction represents amount of AlPI eluted
in each fraction relative to the total.

| SEQ. ID | | Percent AlPI Eluted by Fraction | | |
|---|---|---|---|---|
| NOS. | Sequence | Flowthrough | 1M NaCl | 2% Acetic Acid |
| (a) 4° C. | | | | |
| 37 | VIFLVR | 0 | 3 | 97 |
| 61 | RVLFIV | 8 | 27 | 65 |
| 62 | RVLFIH | 0 | 29 | 71 |
| 61 | Ac-RVLFIV | 76 | 11 | 13 |
| (b) 20° C. | | | | |
| 37 | VIFLVR | 0 | 7 | 93 |
| 61 | RVLFIV | 7 | 3 | 90 |
| 62 | RVLFIH | 0 | 3 | 97 |
| 61 | Ac-RVLFIV | 19 | 31 | 50 |

TABLE 19

A1PI Purification for VIFLVR Sequence Order
Mass balance for columns based on the injection of 5 mg hSA + 1 mg A1PI at
4 and 20° C. The masses are based on immunonephelometry. Percent Eluted
by Fraction values in parentheses are protein-specific and represent the amount
of the given protein eluted in the fraction relative to the total loaded.

| SEQ ID | Peptide | | Mass Protein per Eluate Fraction, mg (Percent Eluted by Fraction) | | | |
|---|---|---|---|---|---|---|
| NOS. | Sequence | Protein | Flow | 1M NaCl | 3M NaCl | 2% Acetic Acid |
| (A) 4° C. | | | | | | |
| 37 | VIFLVR | A1PI | 0.13 (16) | 0.05 (7) | * (0) | 0.61 (77) |
| | (37) | hSA | 1.84 (38) | 2.87 (60) | * (0) | 0.10 (2) |
| 61 | RVLFIV | A1PI | 0.48 (57) | 0.11 (13) | * (0) | 0.25 (30) |
| | (61) | hSA | 4.40 (75) | 1.44 (25) | * (0) | 0.04 (1) |
| 62 | RVLFIH | A1PI | 0.31 (35) | 0.14 (16) | * (0) | 0.43 (49) |
| | (62) | hSA | 2.38 (40) | 3.46 (59) | * (0) | 0.04 (1) |
| (B) 20° C. | | | | | | |
| 37 | VIFVLR | A1PI | 0.17 (22) | 0.02 (2) | * (0) | 0.60 (76) |
| | (37) | hSA | 4.33 (92) | 0.25 (5) | * (0) | 0.11 (2) |
| 61 | RVLFIV | A1PI | 0.22 (28) | 0.04 (5) | * (0) | 0.54 (68) |

TABLE 19-continued

A1PI Purification for VIFLVR Sequence Order
Mass balance for columns based on the injection of 5 mg hSA + 1 mg A1PI at
4 and 20° C. The masses are based on immunonephelometry. Percent Eluted
by Fraction values in parentheses are protein-specific and represent the amount
of the given protein eluted in the fraction relative to the total loaded.

| SEQ ID | Peptide | | Mass Protein per Eluate Fraction, mg (Percent Eluted by Fraction) | | | |
|---|---|---|---|---|---|---|
| NOS. | Sequence | Protein | Flow | 1M NaCl | 3M NaCl | 2% Acetic Acid |
| | (61) | hSA | 3.70 (64) | 2.05 (35) | * (0) | 0.04 (1) |
| 62 | RVLFIH | A1PI | 0.09 (12) | 0.00 (0) | * (0) | 0.65 (88) |
| | (62) | hSA | 1.14 (22) | 3.92 (77) | * (0) | 0.04 (1) |

* Denotes Below detection limit second positive charge, regardless of position, is important for binding. At 4° C., the sequences RVLFIV (SEQ ID No:61) and RVLFIH (SEQ ID No:62) did not perform as well as VIFLVR (SEQ ID NO:37) in terms of yielding purified A1PI in the acid eluate from an A1PI/hSA mixture.

At both 4° C. and 20° C., acetylation of the N-terminal amino group of RVLFIV (SEQ ID No:61) disrupts binding, especially at 4° C. This result is similar to the N-terminal acetylated sequence Ac-VIFLVR (SEQ ID No:37) which showed similar loss of binding (Table 12).

EXAMPLE 8

Capture and Elution of Active A1PI

The A1PI captured by the peptide columns can be eluted in an enzymatically active form using 2M urea, 0.1M sodium phosphate, pH 6 buffer (Table 20). The columns were loaded with pure A1PI in equilibration buffer at 4° C., then eluted with the 2M urea buffer. Table 20 presents the A1PI mass in the urea eluate as determined by the elastase inhibition activity assay and immunonephelometry. The specific activity in the table represents the mass of A1PI as determined by the activity assay relative to the mass by immunonephelometry. The specific activity for the urea eluates from the peptide columns were about 0.8 mg/mg. Note that the neat starting material of A1PI dissolved in equilibration buffer yielded a specific activity of 0.79 mg/mg, suggesting that no activity has been lost in the binding and elution of A1PI from the peptide columns.

TABLE 20

Elution of Active A1PI from Peptide Columns
Results based on the injection of 1 mg A1PI in equilibration
buffer at 4° C. at a constant flow rate of 523 μl/min
(250 cm/hr). The masses eluted with 2M urea, 0.1M citrate, pH
6 are based on detection by the A1PI elastase inhibition activity
assay and immunonephelometry. The specific activity is given as
the mass of A1PI by activity assay relative to the amount given
by immunonephelometry. Neat A1PI represents the
freshly dissolved A1PI fed to the columns.

| SEQ ID | | Mass A1PI in Urea Eluate (mg) | | Specific Activity* |
|---|---|---|---|---|
| NOS. | Sequence | Activity | Nephelometry | (mg/mg) |
| 3 | RYRIFI | 0.67 | 0.79 | 0.86 |
| 4 | RAFWYI | 0.62 | 0.71 | 0.87 |
| 5 | RFIYYT | 0.67 | 0.80 | 0.84 |
| 7 | LIVHRW | 0.75 | 0.85 | 0.88 |
| 8 | PYWIVR | 0.37 | 0.49 | 0.75 |
| 37 | VIFLVR | 0.36 | 0.45 | 0.81 |

TABLE 20-continued

Elution of Active A1PI from Peptide Columns
Results based on the injection of 1 mg A1PI in equilibration
buffer at 4° C. at a constant flow rate of 523 μl/min
(250 cm/hr). The masses eluted with 2M urea, 0.1M citrate, pH
6 are based on detection by the A1PI elastase inhibition activity
assay and immunonephelometry. The specific activity is given as
the mass of A1PI by activity assay relative to the amount given
by immunonephelometry. Neat A1PI represents the
freshly dissolved A1PI fed to the columns.

| SEQ ID | | Mass A1PI in Urea Eluate (mg) | | Specific Activity* |
|---|---|---|---|---|
| NOS. | Sequence | Activity | Nephelometry | (mg/mg) |
| 62 | RVLFTH | 0.56 | 0.71 | 0.79 |
| | Neat A1PI | 0.87 | 1.10 | 0.79 |

Experiments conducted at 4 and 20° C. showed that active A1PI could be eluted using 4M GdnHCl. Injections of mixtures of A1PI and hSA in equilibration buffer were eluted with 1M NaCl and then 4M GdnHcl. The 4M GdnHCl eluate was diluted 20-fold, concentrated, and assayed by immunonephelometry and A1PI activity assay. The eluate was highly enriched in A1PI, and the A1PI retained its original activity.

CONCLUSION

Peptide sequences with varying degrees of specificity and avidity were identified from the screening of a combinatorial peptide library. A number of sequences including VIWLVR showed the ability to purify A1PI from both aqueous and ethanol-containing feeds. Point mutations of VIWLVR led to an improved sequence for purification, VIFLVR, and identified the key amino acids needed for binding and separation.

The above examples are intended to illustrate the invention and it is thought variations will occur to those skilled in the art. Accordingly, it is intended that the scope of the invention should be limited only by the claims below.

References
Ballieux et al., *J. Immunol. Methods* 159: 63–70 (1993)
Buettner et al., *Int. J. Peptide Protein Res.* 47: 70–83 (1996)
Burnouf et al., *Vox Sang.* 52: 291–297 (1987)
Dubin et al., *Prep. Biochem.* 20: 63–70 (1990)
Hein et al., *Eur. Respir J.* 9: 16s–20s (1990)
Jentoft et al. *Methods in Enzymology* 91: 570–579 (1983)
Kassarjian et al., *Peptide Research* 6(3): 129–133 (1993)
Novika et al., *Gematol Transfuziol.* 34: 46–50 (1989)
Podiarenc et al., *Vopr. Med. Khim.* 35: 96–99 (1989)

Turck *Methods* 6: 396–400 (1994)

U.S. Patents

Bollen et al. U.S. Pat. No. 4,629,567 (1986)
Coan et al. U.S. Pat. No. 4,379,087 (1983)
Coan et al. U.S. Pat. No. 4,439,358 (1984)
Coan U.S. Pat. No. 4,697,003 (1987)
Shearer et al. U.S. Pat. No. 4,656,254 (1987)
Lebing et al. U.S. Pat. No. 5,610,285 (1997)
Hwang et al. U.S. Pat. No. 5,616,693 (1997)
Buettner et al. U.S. Pat. No. 5,723,579 (1998)
Mondorf et al., U.S. Pat. Appl. Ser. No. 09/012,343 (1998).

What is claimed is:

1. A composition comprising a peptide having an available alpha-1 proteinase inhibitor binding domain, wherein the binding domain is selected from the group consisting of Val Ile Trp Leu Val Arg, Ile Ile Trp Lys, Arg Tyr Arg Ile Phe Ile, Arg Ala Phe Trp Tyr Ile, Arg Phe Ile Tyr Tyr Thr, Tyr Lys Phe Arg Phe Trp, Leu Ile Val His Arg Trp, Pro Tyr Trp Ile Val Arg, Ala Arg Trp Tyr Ile His, Gln Tyr His Phe Trp Tyr, Arg Leu Trp Arg Tyr Gly, Val Ile Tyr Leu Val Arg, Val Ile Phe Leu Val Arg, Lys Ile Phe Leu Val Arg, Arg Ile Phe Leu Val Arg, His Ile Phe Leu Val Arg, Arg val Leu Phe Ile Val, or Arg or Val Leu Phe Ile His (SEQ ID NOS: 1–8, 10, 11, 15, 36, 37, 45, 46, 47, 61, and 62 respectively).

2. The composition of claim 1, further comprising alpha-1 proteinase inhibitor bound to the binding domain.

3. The composition of claim 1, wherein the peptide is immobilized upon a water-insoluble support.

4. The composition of claim 3, wherein the support is a chromatography medium.

5. A method of purifying alpha-1 proteinase inhibitor comprising contacting a solution containing alpha-1 proteinase inhibitor with a substrate under conditions sufficient to bind alpha-1 proteinase inhibitor to the substrate, wherein the substrate comprises peptides bound to a support material.

6. The method of claim 5, wherein the peptides have an available alpha-1 proteinase inhibitor binding domain selected from the group consisting of Val Ile Trp Leu Val Arg, Ile Ile Trp Leu Tyr Lys, Arg Tyr Ile Phe Ile, Arg Ala Phe Trp Tyr Ile, Arg Phe Ile Tyr Tyr Thr, Tyr Lys Phe Arg Phe Trp, Leu Ile Val His Arg Trp, Pro Tyr Trp Ile Val Arg, Ala Arg Trp Tyr Ile His, Gln Tyr His Phe Trp Tyr, Arg Leu Trp Arg Tyr Gly, Val Ile Tyr Leu Val Arg, Val Ile Phe Leu Val Arg, Lys Ile Phe Leu Val Arg, Arg Ile Phe Leu Val Arg, His Ile Phe Leu Val Arg, Arg Val Leu Phe Ile Val, or Arg Val Leu Phe Ile His (SEQ ID NOS: 1–8, 10, 11, 15, 36, 37, 45, 46, 47, 61, and 62 respectively).

* * * * *